United States Patent [19]

Applegate

[11] 4,103,365

[45] Aug. 1, 1978

[54] METHOD OF IMPLANTING SYNTHETIC HAIR

[76] Inventor: George D. J. Applegate, 9526 E. Harrison Cir., Tucson, Ariz. 85710

[21] Appl. No.: 702,415

[22] Filed: Jul. 6, 1976

[51] Int. Cl.² ............................................. A61F 1/00
[52] U.S. Cl. ........................................... 3/1; 128/330
[58] Field of Search ........... 3/1; 128/329, 330, 334 R, 128/335.5

[56] References Cited

U.S. PATENT DOCUMENTS

| | | | |
|---|---|---|---|
| 3,553,737 | 1/1971 | Bauman | 3/1 |
| 3,699,969 | 10/1972 | Allen | 3/1 |
| 3,831,202 | 8/1974 | Hulsen | 3/1 |
| 3,858,245 | 1/1975 | Naté et al. | 3/1 |
| 3,914,801 | 10/1975 | Dick et al. | 3/1 |
| 3,998,230 | 12/1976 | Miller | 3/1 X |
| 4,027,675 | 6/1977 | Colone | 3/1 X |

Primary Examiner—Robert W. Michell
Assistant Examiner—Michael H. Thaler
Attorney, Agent, or Firm—J. Michael McClanahan

[57] ABSTRACT

A method of implanting synthetic hair fibers in a person's scalp using a medical suturing needle attached to either one or a plurality of medically inert synthetic hair fibers having knots tied in the length of fiber at intervals of about ten inches. The fiber is threaded in serpentine fashion through a person's scalp below the skin where the knots are left in the third skin layer. The loops formed by the fibers above the skin are subsequently cut at their approximate center and/or the end proximate the needle so that the resultant appearance is that of a normal head of hair. The skin heals about the implanted fiber and holds it in place.

12 Claims, 7 Drawing Figures

METHOD OF IMPLANTING SYNTHETIC HAIR

BACKGROUND OF THE INVENTION

The search of men and women for methods or replacing hair in the scalp or otherwise camouflaging baldness is well known. There presently exist many methods attempting to replace the loss of hair or to implement means providing functions of holding hairpieces or wefts of hair close to the scalp. For example, it is commonly known that hair may be removed from various parts of the body and transplanted, together with the surrounding skin, in the scalp of a person with the hope that the transplant will thrive and continue growing. This method, while extremely expensive, has not been noticeably successful.

There have been numerous other methods of attempting to present the appearance of hair in the scalp by such means as laboriously inserting a hair, or a fiber, into the skin by boring a hole in the scalp and locating the hair or fiber within that bore. The most prevalent method of advancing the appearance of hair has been in the field of attaching devices to the scalp to which in turn are attached wefts of synthetic or human hair made into wigs or hairpieces. These methods may comprise sutures in the person's scalp through which threads are run to secure mechanical holding devices to which the hairpiece is attached. These mechanical devices comprise in themselves quite complex mechanical fasteners. Therer are other methods which have been so simple as to merely intertwine the ends of the thread suture and attach hair wefts to these threads.

The above methods which utilize mechanical or other holding devices for the hairpieces or wefts of hair suffer from many shortcomings such as the need for periodic tightening of the means holding the mechanical fastening device close to the scalp in addition to the possibilities of infection resulting from the closeness of the mechanical device to the area of the scalp.

SUMMARY OF THE INVENTION

The present invention comprises a method whereby synthetic hair fibers are implanted below the surface of a person's scalp which results in the fiber emerging from the scalp having the appearance of natural hair growing. A fiber is selected which is medically inert to the skin of the scalp and about which the skin will heal. This fiber is first threaded through a stainless steel medical suturing needle having an eye and knots are tied in the fiber at intervals of every ten inches or so in the length of fiber. The knots are left below the skin in the third skin layer and the loops are cut at the lengths desired. As a result, for each stitch in the scalp two synthetic hair fibers emerge from the scalp which, upon the passage of time, the skin heals around and completely encloses the fiber and the knot in the fiber resulting in strong, removal-resistant, hair-appearing strands of fiber.

Accordingly, it is an object of the present invention to provide a method of implanting synthetic hair fibers below the scalp to appear as hair particles.

It is also an object of the present invention to provide a method of implanting a plurality of hair-appearing synthetic fibers in a plurality of divers places in a person's scalp which give the appearance of growing hair.

DETAILED DESCRIPTION

The embodiment of the invention shown in FIG. 1 illustrates the synthetic hair fiber material which is prepared for implantation into a person's scalp. Specifically, at least one medically inert synthetic hair fiber strand 10 is threaded through the eye of a stainless steel suture needle 12 and the fiber doubled back. A plurality of knots 14 are tied at intervals of approximately 10 inches, the first and last knots being about 5 inches from the surgical needle and the end of the synthetic hair fiber 10 respectively.

Figure 1A:
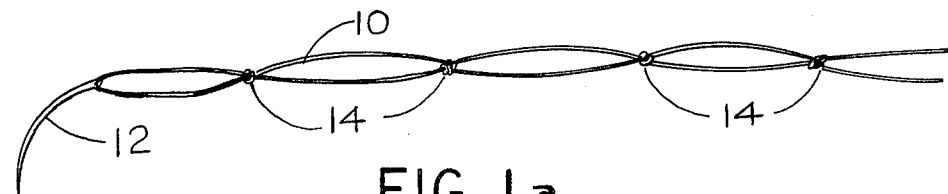
FIG. 1a is a drawing of the synthetic hair fiber in preparation for implanting.
Figure 1B:
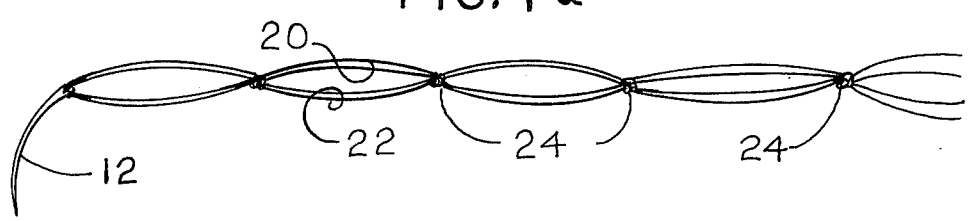
FIG. 1b is a drawing of a plurality of synthetic hair fibers in preparation for implanting.

Shown in FIG. 1b is the alternate construction of the needle 12 and synthetic hair fibers to be implemented where a plurality of fibers 20 and 22 are threaded through the needle, having the knots 24 tied in the ten-inch-interval fashion as shown in FIG. 1a. It has been determined that many fibers may be threaded through the needle, doubled over, and returned until the ends join and then the knots tied as the fibers are of diameters similar with human hair. As many as eight fibers have been tried although this is not limiting.

It has been found that the knots which are formed in the fibers are smaller than the shaft of the suture needle because of the relative thinness of the fibers. This makes the job for the operator easier since the suture needle has opened up a passageway through the skin and the fiber is easily drawn through. This, of course, is not a limiting factor as a knot larger than the needle could be pulled through the formed hole.

Figure 2:
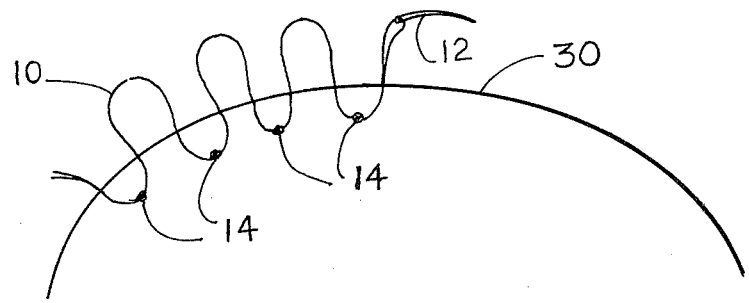
FIG. 2 is a cross-sectional view of the implementation of the synthetic hair fibers into a person's scalp.

Reference now to FIG. 2 illustrates the implementation of the synthetic fibers into the person's scalp where the needle 12 and fiber assembly 10 of FIG. 1 is threaded in serpentine fashion beneath the surface of the scalp 30 and into the third skin layer, the subcutaneous fatty tissue and the same area that a hair follicle is located.

In the inventive process of implanting synthetic fibers beneath the scalp, the scalp 30 is first prepared by cleaning thoroughly with an antiseptic-type soap solution and thereafter drying the scalp. Thereafter, an isopropyl alcohol bath is performed upon the scalp and the residual alcohol is permitted to evaporate. The next step comprise the application of a local anesthetic, such as Novacaine or Xylocaine, which is applied to the scalp by injecting into the skin and permitted to anesthetize the skin layers in the area upon which fibers are to be inserted.

After the initial cleansing operations are completed, needles and the threaded fibers are sterilized by using presterilized needles followed by placing the assembly into a steam chamber or alcohol bath for a sufficient length of time to become sterilized. In most instances, the once sterilized needles become unsterilized when the fibers are threaded through the eye and thus need the sterilization process repeated.

It has been found in practice that the preferred method of inserting the needle through the person's scalp is to draw up a portion of the scalp between the operator's fingers, such as to pinch the scalp, and then using surgical clamps to hold the needle, penetrate one side of the pinched scalp skin to the other with the needle making sure the needle goes into the third skin layer. The needle is then pulled through the scalp skin and the fibers also pulled through until the last knot on the fiber string goes below the skin into the skin's third layer, the subcutaneous fatty tissue, where it is permitted to remain. The knot is left at that point and the operator moves on to make the next stitch. Note that at this point the synthetic fiber appears to be emerging from two different spaced apart places upon a person's scalp, which, have been found in practice to be nominally one quarter inch apart, the knot being in the center. This distance may be varied in accordance with the hair density desired.

After the first stitch has been made, the operator proceeds on to the second stitch which, in the preferred embodiments, is normally spaced about a quarter of an inch from the point at which the fiber emerged from the last stitch. Again, the scalp is grasped between the operator's fingers in a pinching-type mode, and the suture needle inserted through the pinch of skin to emerge on the opposite side pulling with it the strand of synthetic hair fiber. Also again the fiber is pulled through the hole created by the needle until the then last knot is inserted under the skin and left in the third skin layer. The process is then repeated until all knots have been left under the skin by the plurality of stitches and the fiber cut near the suture needle and the needle removed. The loops which have been created are also cut at their centers which results in two synthetic hair fibers appearing to emerge from the scalp.

Figure 3:
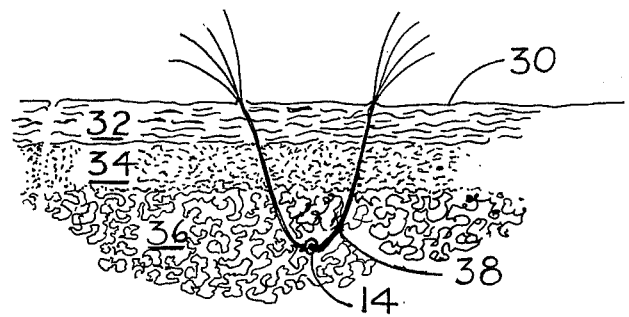
FIG. 3 is an enlarged cross-sectional view of one implementation of the synthetic hair fibers into a person's scalp.

FIG. 3 is a cross-sectional view of a person's scalp with the synthetic hair fiber located below the scalp. In the Figure, the person's scalp 30 is shown with the plurality of synthetic hair fibers 38 emerging from the surface. As seen in FIG. 3, fibers 38 pass through the first skin layer 32, the epidermis, through the second skin layer 34, the corium, and into the third skin layer 36, the subcutaneous fatty tissue where knot 14 is located. After the fibers are in place a short period of time the skin heals around them and thus forms a barrier to infection. In practice, it has been found that there are times when the suture needle will penetrate small blood vessels in the skin layers in which case the blood may come to the surface of the scalp and require removal. The blood normally coagulates and ceases to be a problem thereafter.

Figure 4:
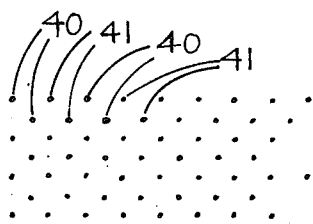
FIG. 4 is a pattern of implementing the synthetic hair fiber into a person's scalp.

In the preferred embodiment the pattern which the stitches take in a person's scalp is as drawn in FIG. 4. Here, the stitches in a horizontal row may be taken by the one continuous operation of a single fiber strand assembly, there being approximately one quarter inch from each entrance 40 and exit 41 of the synthetic hair fiber. The second horizontal pattern line also has one quarter inch spacing between subsequent entrances 40 and exits 41 of the synthetic fiber, however, as can be seen from FIG. 4, each entrance and exit of the fiber is about one eighth of an inch from an imaginary line drawn through the first pattern row and spaced equally from the entrances and exits of the first pattern row. Thereafter, in the third row, the spacing is again repeated as in the first row and the position of the third row relative to the second row is the same as the first row relative to the second row. This pattern is continued until the area which is desired to be implanted has been filled in. It is realized that this spacing produces one density of fibers and another density may be had by varying the distance between entrances and exits.

Figure 5:
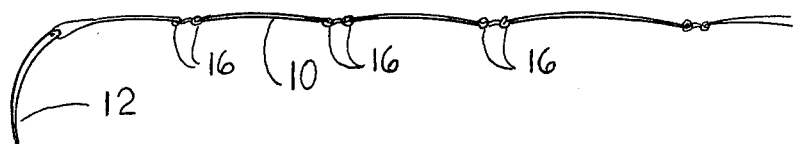
FIG. 5 is an alternate embodiment of the synthetic hair fiber in preparation for implanting.

FIG. 5 shows an alternate embodiment of the distribution of knots on the synthetic fiber where the single knot at 10 inch spacing has been replaced with a plurality of knots 16 very closely spaced, such as one sixteenth inch or less, still maintaining, however, the average spacing of 10 inches between the pair of knots. In utilizing the fiber strand make-up of FIG. 5, both knots 16 are left below the skin in the third layer and do provide some extra protection against the strand being accidentally pulled out, for example, when brushing or combing the hair.

Figure 6:
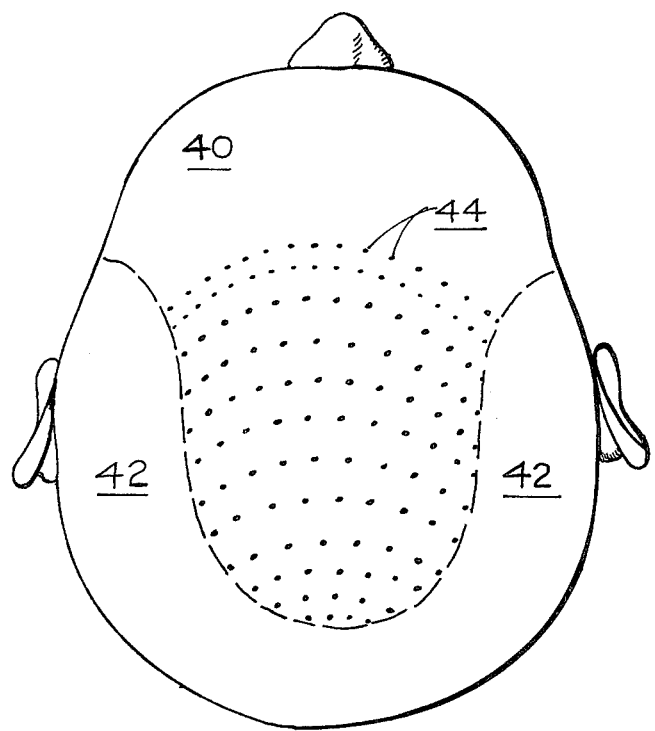
FIG. 6 is a top view of a person's scalp showing the pattern used for implementing the synthetic hair fibers into a person's scalp bald area.

Referring now to FIG. 6, a typical balding head is shown in a top view where the person's scalp 40 has been partially depleted of hair, there remaining only the natural hair area 42. Here, shown as dots 44, is the pattern one may follow to implant the synthetic hair fibers by the process herein disclosed so as to duplicate the person's original hair line.

In the usual process of implanting the synthetic hair fibers, a portion of the person's scalp is selected for implants for one sitting at which time that portion is anesthetized as earlier described and hair implanted.

After all implantations have been accomplished for that sitting, the area of the scalp which has been worked is first rinsed with warm running water, allowed to dry, and then disinfected by means of hydrogen peroxide or other antiseptic. If hydrogen peroxide is used, it should not remain on the area for a time long enough to bleach the synthetic hair fibers or, for that matter, living hair which may be nearby. Thereafter, the antiseptic is rinsed off and the scalp area thoroughly washed. A hair conditioner may be applied to the synthetic hair fibers as it has been found that these fibers used in the preferred embodiment do respond to hair conditioners similarly as does hair.

Between sittings, the scalp may be dabbed with alcohol-soaked cotton swabs to help prevent infection and to form scabs around the entrances and exits of the fiber helping the skin in its process of healing.

The number of sittings required for a person is directly dependent upon the amount of area which is wished to be covered with the synthetic hair fibers. In those areas of the scalp in which an especially thick appearance of hair is desired, it is possible to return to areas previously implemented and intersperse fibers between the already existing fibers.

It is suggested that the time between sittings should allow for complete healing of prior implantation.

Techniques which have proven successful in attempting to imitate the appearance of hair and hair sytle utilized by the operator in performing the inventive process herein described are to vary the distance between the knots so that longer or shorter fiber strands are created as is desired. Obviously, there is no limit to the length of fiber utilized and thus to the length of imitation hair created. Additionally the thickness of the fibers used may be blended throughout the scalp as is a person's normal hair. This may be accomplished by utilizing different rows of entrances and exits, each row having a different thickness of hair, or by varying the thickness of the fiber strands in the plurality of strands which are threaded through the suture needle as already described. Further, color blending may be accomplished, for instance, by placing different colored fiber strands at various points in the person's scalp, or by blending different colored fibers in the multiple fiber strand assembly as was done for different thicknesses of the fiber strands.

As has been touched upon earlier in this specification, the subject inventive process may be used to place the synthetic hair fibers in areas of the scalp where the normal hair has begun thinning. In this case, by careful color blending with the natural hair, and with a sufficient look-alike synthetic fiber, it will be impossible to distinguish between the normal hair and the imitation hair.

In the preferred embodiment, the material which has been utilized as the synthetic hair fiber is a modacrylic fiber. Other fibers which have the required properties which have been described, such as being medically inert to the skin, may be utilized. One such fiber is Marlex manufactured by the Phillips Petroleum Company. The properties of the fiber such as various colors, varying thicknesses, and having characteristics similar to hair in regard to such things as curling, are all desirable esthetic properties, but which are not necessary to the practice of this invention.

It is to be realized, of course, that while synthetic hair fibers have been discussed in this specification, animal or human hair can be utilized providing that such hair is inert so far as implanting below human skin is concerned, or has been treated to render the hair inert.

While a preferred embodiment together with alternate embodiments have been described, these embodiments are not intended to cover all modifications and alternate constructions falling within the spirit and the scope of the invention as defined in the appended claims.

I claim:

1. A method for implanting synthetic hair fiber into living skin tissue comprising the steps of attaching synthetic hair fiber to a needle; tying at least one knot in the synthetic hair fiber; passing the needle under the skin tissue into the subcutaneous tissue layer such that separate entrance and exit points are made; drawing the synthetic fiber through the skin tissue; leaving the portion of the synthetic fiber having the knot under the skin; and separating the needle from the synthetic fiber whereby the synthetic fiber emerging from the skin tissue creates the appearance of living hair.

2. The method of implanting synthetic hair as defined in claim 1 wherein the step of leaving the portion of the synthetic fiber having the knot under the skin comprises the step of leaving the portion of the synthetic fiber having the knot in the subcutaneous tissue level.

3. The method for implanting synthetic hair as defined in claim 2 wherein the step of tying at least one knot in the synthetic hair fiber comprises tying a plurality of spaced apart knots in the synthetic hair fiber.

4. The method for implanting synthetic hair as defined in claim 3, wherein the step of passing the needle under the skin tissue into the subcutaneous tissue layer comprises passing the needle under the skin tissue into the subcutaneous tissue layer in a plurality of spaced apart locations in serpentine fashion, leaving one of the plurality of knots in the subcutaneous tissue layer in each of the skin tissue penetrations, and cutting the loop of fiber between each tissue penetration.

5. The method of implanting synthetic hair as defined in claim 4 wherein the step attaching the synthetic hair fiber to a needle comprises the step of attaching a plurality of synthetic hair fibers to a needle.

6. The method for implanting synthetic hair as defined in claim 5 wherein the step of attaching a plurality of synthetic hair fibers to a needle comprises the step of attaching a plurality of fibers of different thicknesses.

7. The method for implanting synthetic hair as defined in claim 5 wherein the step of attaching a plurality of synthetic hair fibers to a needle comprises the step of attaching a plurality of fibers of different colors.

8. The method for implanting synthetic hair as defined in claim 6 wherein the step of tying a plurality of spaced apart knots in the synthetic hair fiber comprises the step of tying a plurality of pairs of knots, the pairs of knots spaced closely together widely separated from other pairs of closely spaced together knots, and leaving one of the pairs of knots in the subcutaneous tissue in each skin tissue penetration.

9. The method for implanting synthetic hair as defined in claim 1 wherein the step of attaching synthetic hair fiber to a needle comprises the step of attaching synthetic hair fiber medically inert to living skin tissue to a needle.

10. The method for implanting synthetic hair as defined in claim 9 wherein the step of attaching synthetic hair fiber medically inert to living skin tissue to a needle comprises the step of attaching modacrylic fiber to a needle.

11. A method for implanting hair fiber into living skin tissue comprising the steps of attaching treated medically inert animal hair to a needle; tying at least one knot in the hair; passing the needle under the skin tissue into the subcutaneous tissue layer such that separate entrance and exit points are made; drawing the hair through the skin tissue; leaving the portion of the hair having the knot under the skin; and separating the needle from the hair whereby the hair emerging from the skin tissue creates the appearance of living hair.

12. The method for implanting hair as defined in claim 11 wherein the step of attaching treated medically inert animal hair to a needle comprises the step of attaching treated medically inert human hair to a needle.

* * * * *

UNITED STATES PATENT AND TRADEMARK OFFICE
CERTIFICATE OF CORRECTION

PATENT NO. : 4,103,365
DATED : August 1, 1978
INVENTOR(S) : George D. J. Applegate It is certified that error appears in the above-identified patent and that said Letters Patent are hereby corrected as shown below:

In the claims, Claim 8, line 2, reference numeral "6" should read --4--.

Signed and Sealed this

Twentieth Day of March 1979

[SEAL]

Attest:

RUTH C. MASON
Attesting Officer

DONALD W. BANNER
Commissioner of Patents and Trademarks